United States Patent [19]

Inoue

[11] 4,245,123
[45] Jan. 13, 1981

[54] METHOD FOR MANUFACTURING AN OXIDIZING AGENT AND METHOD FOR USING THE OXIDIZING AGENT

[75] Inventor: Makoto Inoue, Tokyo, Japan

[73] Assignee: Sony Corporation, Tokyo, Japan

[21] Appl. No.: 956,406

[22] Filed: Oct. 31, 1978

[30] Foreign Application Priority Data

Nov. 2, 1977 [JP] Japan .................................. 52/131832

[51] Int. Cl.³ ............................................ C07C 179/00
[52] U.S. Cl. ...................................... 568/577; 568/571
[58] Field of Search ................................ 568/571, 577

[56] References Cited

FOREIGN PATENT DOCUMENTS 638661 3/1962 Canada ..................................... 568/571

*Primary Examiner*—Werren B. Lone
*Attorney, Agent, or Firm*—Hill, Van Santen, Steadman, Chiara & Simpson

[57] ABSTRACT

A method of manufacturing an oxidizing agent comprises the step of oxidizing polyoxyalkylene having an average molecular weight of 1,000 to 30,000 and being represented by the following general formula:

$$+R-O+_n$$

where R stands for alkylene group represented by $(CH_2)_m$ where $m = 2$ or $3$. A solution such as an aqueous solution containing polyoxyalkylene of more than 1% by weight, or a melted polyoxyalkylene is treated by supplying an oxidizing gas thereinto to oxidize and decompose the polyoxyalkylene into the oxidizing agent. A method of oxidation by the use of the oxidizing agent manufactured by the above-described method is applied to, for example, a surface treatment of semiconductor or metal.

1 Claim, 11 Drawing Figures

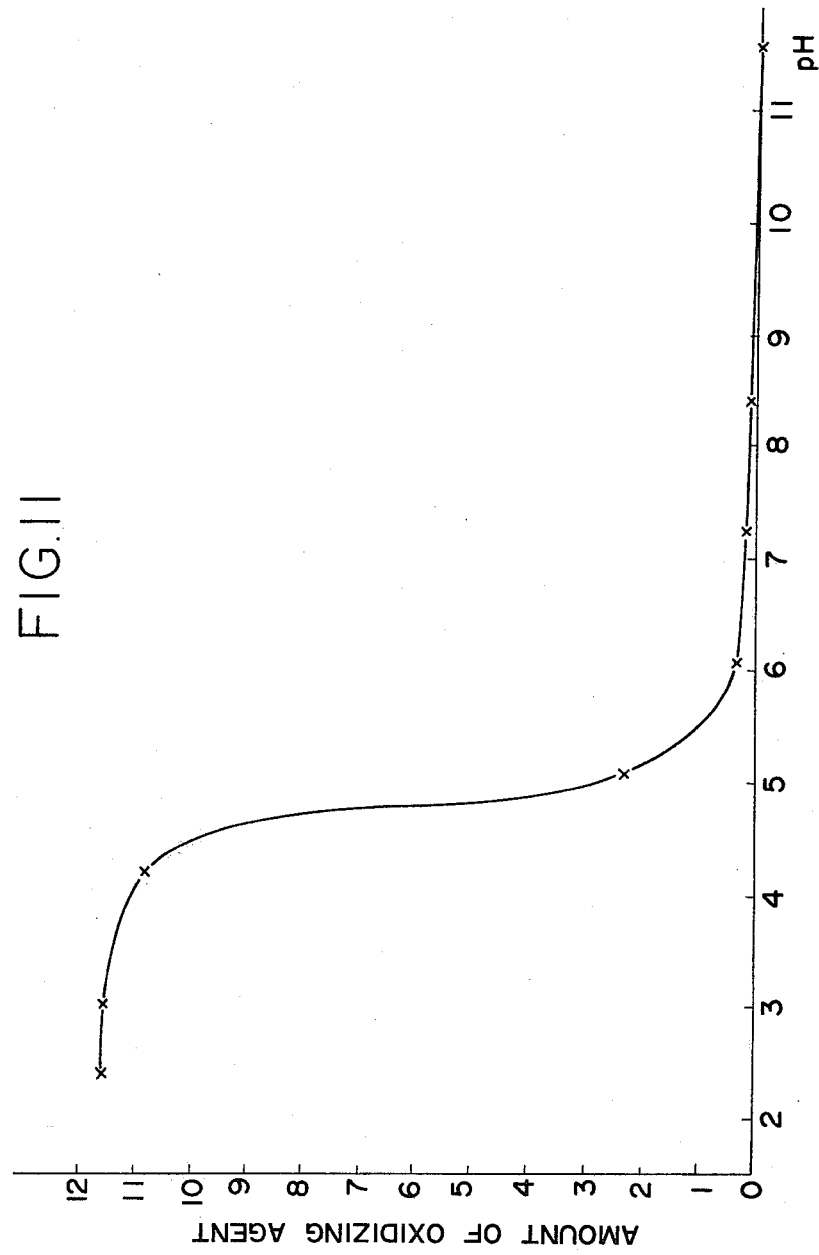

METHOD FOR MANUFACTURING AN OXIDIZING AGENT AND METHOD FOR USING THE OXIDIZING AGENT

BACKGROUND OF THE INVENTION

1. Field of the Invention

This invention relates to a method of manufacturing an oxidizing agent which is obtained by oxidation of polyoxyalkylene. This invention relates also to a method of oxidation by the use of the oxidizing agent manufactured by the above-described method.

2. Description of the Prior Art

The conventional typical oxidizing agents mostly contain a harmful metal like bichromate and permanganate, or are unstable at a room temperature like hydrogen peroxide solution and ozone. These conventional oxidizing agents are accordingly undesirable in view of safety and stability. According to the known chemical oxidation method which has been used for forming a surface oxidized layer on GaAs being a compound semiconductor material, the growing velocity of the oxidized layer is slow and an oxidized layer having an even thickness can not be obtained. On the other hand, as for an oxidation of polyoxyalkylene, the oxidation reaction of polyoxyalkylene without difficutly and the resulting oxidizing product are known from "pharm. Acta. Helv.", volume 50, page 10 (1975) by R. Hamburger, E. Azaz and M. Donbrow.

SUMMARY OF THE INVENTION

An object of this invention is to manufacture very easily an organic oxidizing agent which is stable and harmless and has a good long preservation property.

Another object of this invention is to provide an oxidizing agent having a superior oxidizing power.

A still further object of this invention is to provide a method of oxidation whereby an oxidized layer having an even thickness can be formed at a low temperature and for a short time.

In accordance with this invention, the method of manufacturing the oxidizing agent comprises the step of oxidizing polyoxyalkylene which is of a polyether type being represented by the following general formula:

where R stands for alkylene group represented by $(CH_2)_m$. Polyoxyalkylene to be used for this invention is polyethylene glycol (M=2) or polyprolylene glycol (M=3) and has an average molecular weight (weight-average molecular weight) of 1,000 to 30,000. According to this invention, such polyoxyalkylene is oxidized in a liquid state to produce the oxidizing agent, that is, a solution such as an aqueous solution of polyoxyalkylene of more than 1% by weight, or a melted 100 percent polyoxyalkylene containing no solvent is oxidized by blowing an oxidizing gas thereinto. In this case, it is preferable to effect the oxidation reaction of polyoxyalkylene at a temperature above 5° C. from the view point of the reaction velocity. The oxidation reaction in the above-described aqueous solution should be effected at a temperature below the boiling point. It is more preferable that the temperature for the oxidation reaction is practically below 100° C. for any of the aqueous solution of polyoxyalkylene and the melted polyoxyalkylene.

According to this invention, it is supposed that when the oxidizing gas comprising oxygen ($O_2$), ozone ($O_3$) or these mixture is blown or passed into the polyoxyalkylene solution or the melted polyoxyalkylene, at least a part of polyoxyalkylene is oxidized and the bonding chains of polymer thereof are cut off to produce organic peroxide, carboxylic acid and the like. The resulting organic oxidizing agent contains the organic peroxide and the like which are supposed to exhibit an oxidizing function. Hydrogen peroxide, hydrogen peroxide solution or air can be used as the oxidizing agent for the oxidation of polyoxyalkylene.

According to a preferred embodiment of this invention wherein an article or substrate is oxidized with the oxidizing agent manufactured by the above-described method, the article or substrate is oxidized at a temperature in the range of 50 to 100° C. in such condition that the oxidizing agent is a liquid state is kept under an acidity of less than pH value of 5.0.

BRIEF DESCRIPTION OF THE DRAWINGS

FIG. 11 is a graph showing a relationship between pH value of the resulting solution of the oxidizing agent and amount of the oxidizing agent.

DESCRIPTION OF THE PREFERRED EMBODIMENTS

The method of this invention will be described in detail with reference to the following experimental examples § Experimental equipment to be used for manufacturing oxidizing agent.

Figure 1:
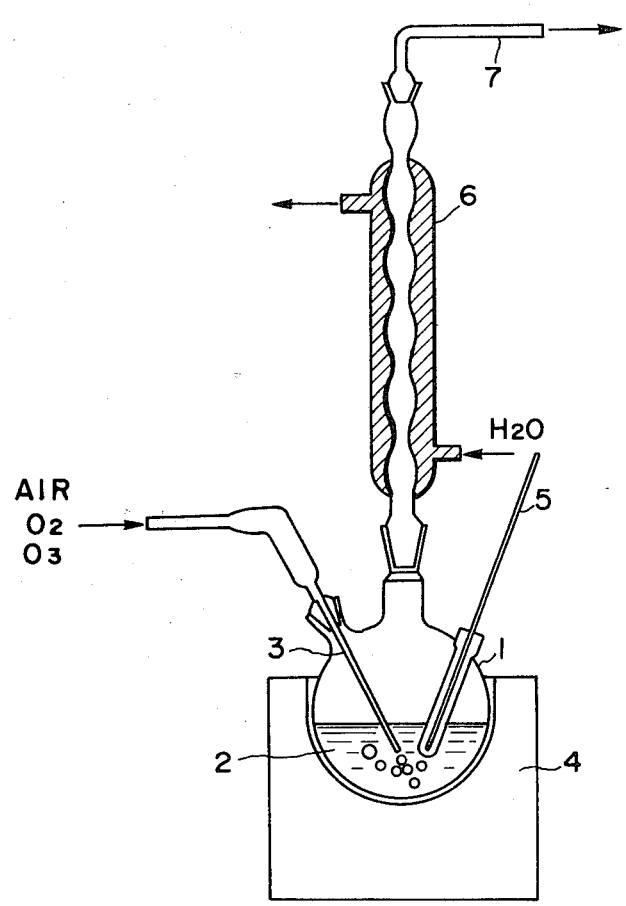
FIG. 1 is a schematical cross-sectional view showing an experimental equipment to be used for manufacturing the oxidizing agent according to this invention.

An experimental equipment as shown in FIG. 1 was used. In this equipment, an aqueous solution 2 of the polyoxyalkylene was received in a reaction vessel 1. Oxidation reaction was effected in such condition that $O_2$ and/or $O_3$ were blown into the solution 2 through a conduit 3 and the solution 2 was heated by a mantle heater 4. The heating temperature was measured by a thermometer 5. Vapours rising from the vessel 1 were cooled in a reflux condenser 6 to discharge only unnecessary vapours from a conduit 7. $O_2$ which was blown into the solution 2 might be supplied as air.

As a result of the oxidation reaction by the use of the above-described reactor, water-soluble oxidizing agent as product remained in the reaction vessel 1.

§ Treating time by oxygen ($O_2$) and amount of oxidizing agent produced.

There was prepared respective 2% by weight aqueous solution of polyethylene glycol (hereafter called "PEG") having an average molecular weight of 1,540 (PEG 1,540 on sale manufactured by Wako Junyaku Corp.), PEG having an average molecular weight of 4,000 (PEG 4,000 on sale manufactured by Wako Junyaku Corp.) and PEG having an average molecular weight of 20,000 (PEG 20,000 on sales manufactured by Wako Junyaku Corp.). Each 200 ml of these aqueous solution was contained in the reaction vessel. The oxidation reaction was effected for the treating time of 30 minutes, 1 hour, 2 hours, 4 hours, 6 hours and 8 hours respectively for each aqueous solution under constant conditions that the flow rate of oxygen ($O_2$) was 200 ml/min and the temperature was 94° C. Each aqueous solution of PEG was treated for 2 hours by introducing a mixture of oxygen ($O_2$) and ozone ($O_3$) thereinto.

After each pH value of the solutions of the oxidizing agents produced was measured, 20 ml of the solution was poured into a beaker having a volume of 100 ml. This solution was added by 0.1 mol KI solution and then left for 12 hours. When 0.01 mol $Na_2S_2O_3$ solution was dropped into the solution in which free iodine ($I_2$) was released from KI in the beaker, to dilute the color of the solution into weak yellow, a starch solution was added thereto. The solution in the beaker was then titrated until the blue color thereof disappeared. This operation was effected also in the below-described experimental examples.

Figure 2:
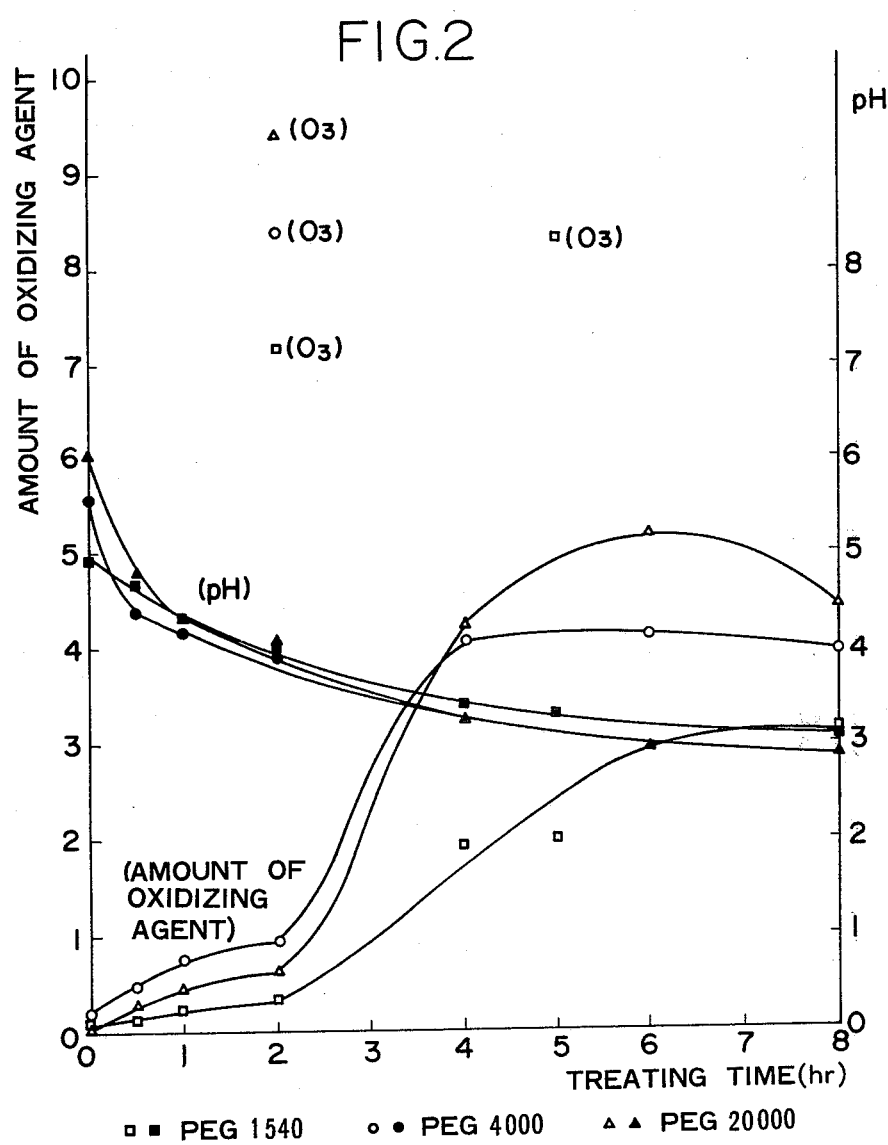
FIG. 2 is a graph showing respective change of amount of the oxidizing agent produced and pH value of the solution in dependence on a treating time by oxygen ($O_2$)

The amount (ml) of the 0.01 mol $Na_2S_2O_3$ solution required to neutralize the free or isolated $I_2$ was represented as an amount of the oxidizing agent produced (hereafter simply called "amount of the oxidizing agent" or "oxidizing agent produced"). FIG. 2 shows respective change of the amount of the oxidizing agent and pH value of the solution in dependence on the treating time for the solution.

According to the result shown in FIG. 2, the pH value indicated by black dots decreases as the treating time increases. Besides, the amount of the oxidizing agent indicated by white dots changes abruptly in a boundary range of the treating time from 2 hours to 4 hours, and increases until the treating time of about 6 hours and decreases again therefrom. This fact shows or suggests that the oxidation process of this invention includes one stage wherein chemical structures different from the starting materials are produced in the process of producing the oxidizing agent, and that the oxidizing agent is an intermediate product at the time when alcohol changes into carboxylic acid. In any cases, the treating time of 4 to 6 hours is necessary for obtaining the oxidizing agent with high yield by the oxygen oxidation, and the use of PEG having a higher molecular weight results in good yield of the oxidizing agent.

Figure 3:
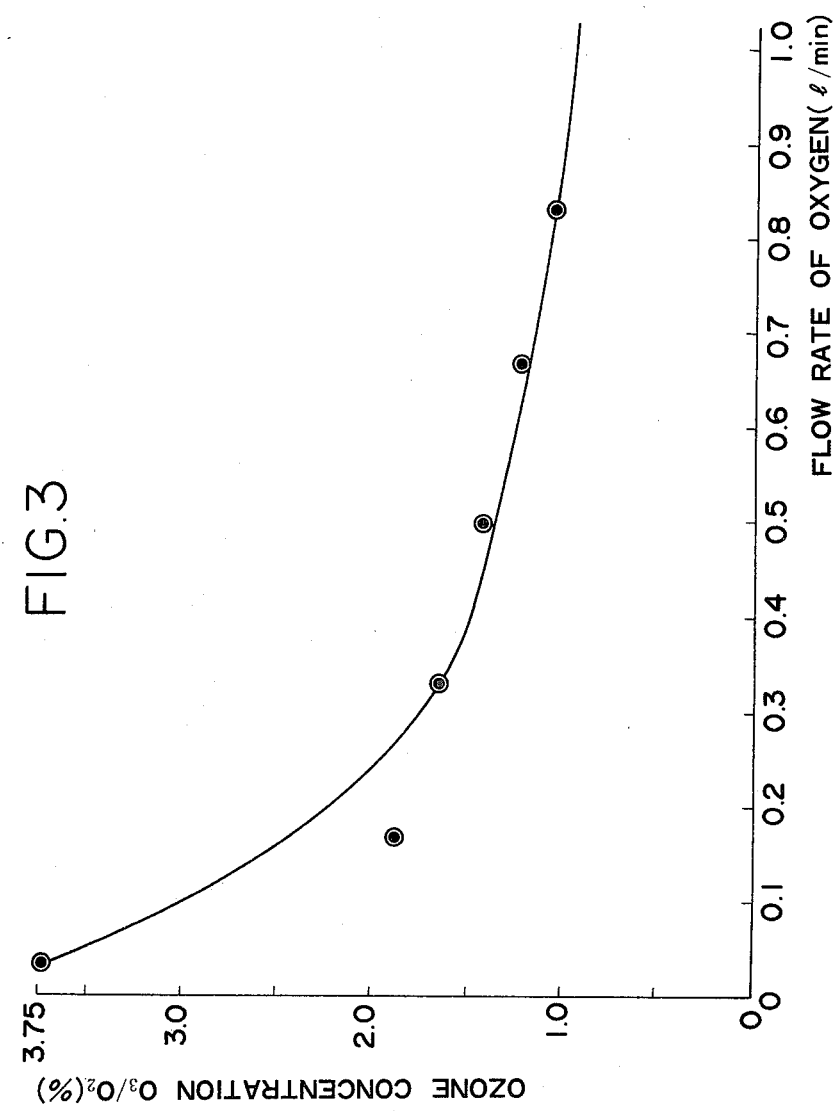
FIG. 3 is a graph showing a relationship between a flow rate of oxygen ($O_2$) introduced into an ozone generator and a concentration of the resulting ozone ($O_3$)

Besides, in the case that a mixed gas of oxygen ($O_2$) and ozone ($O_3$) wherein the ratio $O_3/O_2$ was about 2% was supplied into the solution of PEG under the similar condition to that described above, the amount of the oxidizing agent produced is indicated by the mark Δ ($O_3$), O ($O_3$) or □ ($O_3$) as shown in FIG. 2. FIG. 2 teaches that the oxidation by the mixed gas results in higher yield of the oxidizing agent than the oxygen oxidation, and that PEG having a higher molecular weight results in good yield like the oxygen oxidation. The mixed gas was produced by the known ozone generator, for example, the 0-1-2 type generator manufactured by Nippon Ozone Corp. FIG. 3 shows the relationship between a flow rate of oxygen ($O_2$) supplied to the known generator and an amount of ozone produced, that is, a ratio $O_3/O_2$.

§ Molecular weight of PEG and amount of oxidizing agent produced.

Respective 2% by weight aqueous solution of PEG 200 (average molecular weight of 200), PEG 1,000 (average molecular weight of 1,000), PEG 1540, PEG 2,000 (average molecular weight of 2,000), PEG 4,000, PEG 6,000 (average molecular weight of 6,000), PEG 20,000 and ethylene glycol was treated with a mixture of oxygen ($O_2$) and ozone ($O_3$) for 2 hours under a condition that the ratio $O_3/O_2$ was about 2%, the flow rate of the mixture was 200 ml/min and the temperature of the solution was about 100° C. The relationship between the molecular weight of PEG and ethylene glycol and the amount of the oxidizing agent produced is shown in FIG. 4 in which each numeral noted at the dots for the measured amount of the oxidizing agent means the pH value of the solution of the oxidizing agent.

Figure 4:
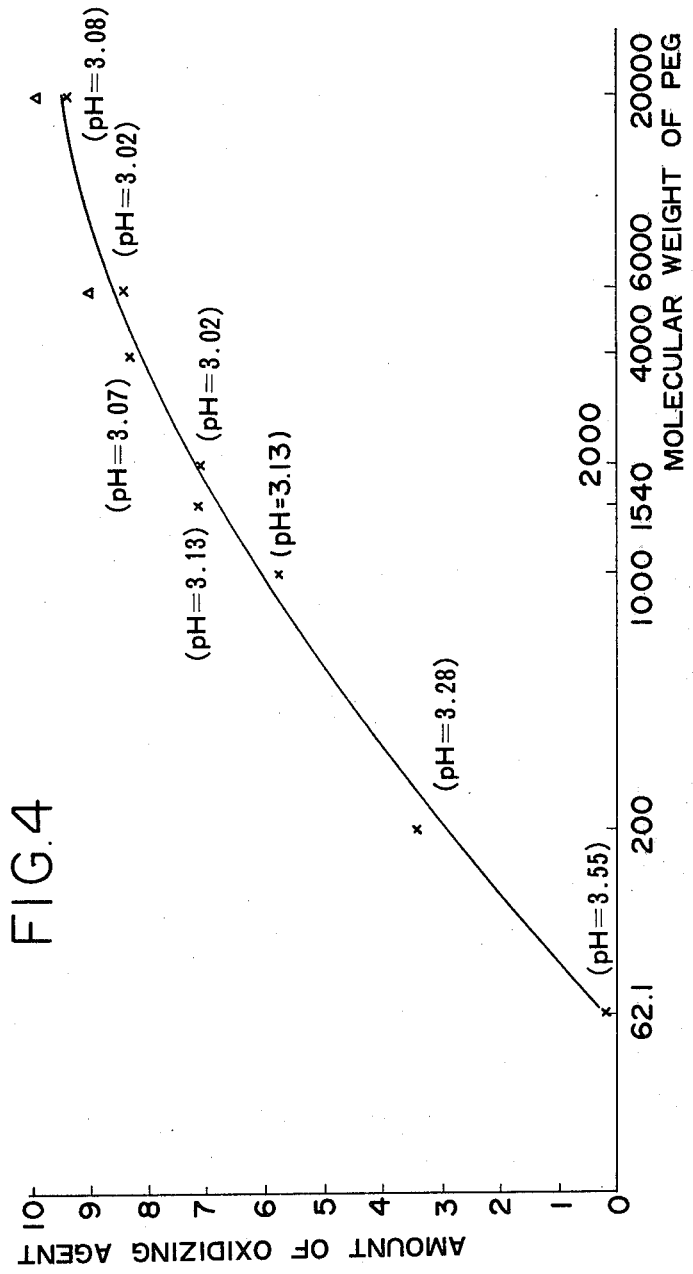
FIG. 4 is a graph showing a relationship between amount of the oxidizing agent produced and molecular weight of polyethylene glycol being a raw material.

According to the result shown in FIG. 4, it will be understood that PEG having a molecular weight results in a higher yield of the oxidizing agent. The pH value of the solution seems to tend to somewhat decrease as the molecular weight of PEG increases, however, the pH value is supposed in particular not to have relations with the molecular weight. The molecular weight of PEG to be used is preferably in the range of 1,000 to 30,000. This is because PEG is hard to be oxidized so that the oxidizing power of the oxidizing agent is weakened when the molecular weight is below 1,000, and the solubility of PEG to water is lowered so that the amount of the oxidizing agent is liable to saturate when the molecular weight is above 30,000.

The data for the oxidizing agents which were manufactured by the substantially similar way to that described above and which were left for six months are indicated by the mark Δ. Each amount of these oxidizing agents does not substantially differ from that of the oxidizing agent which was obtained immediately after being manufactured. This facts shows that the oxidizing agent of this invention is stable.

§ Treating time by ozone ($O_3$) and amount of oxidizing agent manufactured from PEG 20,000

Figure 5:
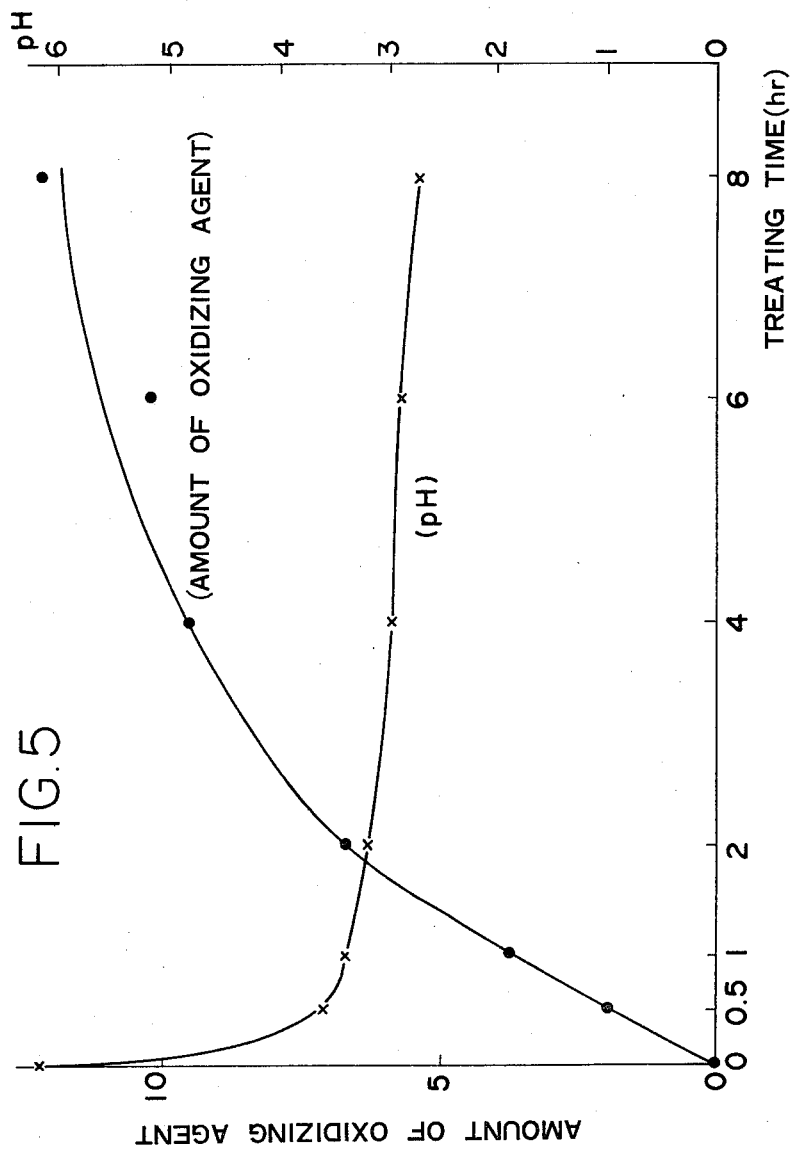
FIG. 5 is a graph showing respective change of amount of the oxidizing agent produced and pH value of the solution in dependence on a treating time by a mixture of oxygen ($O_2$) and ozone ($O_3$)

2% by weight aqueous solution of PEG 20,000 was treated with a mixed gas of $O_2$ and $O_3$ for 30 minutes to 8 hours under the condition that the flow rate of oxygen introduced into the ozone generator was 200 ml/min and the ratio $O_3/O_2$ in the mixed gas was about 2%. According to the result shown in FIG. 5, it can be understood that the amount of the oxidizing agent in the solution increases with the treating time while the pH value of the solution decreases with the treating time.

§ Flow rate of mixed gas of $O_3$ and $O_2$ and amount of oxidizing agent manufactured from PEG 20,000

Figure 6:
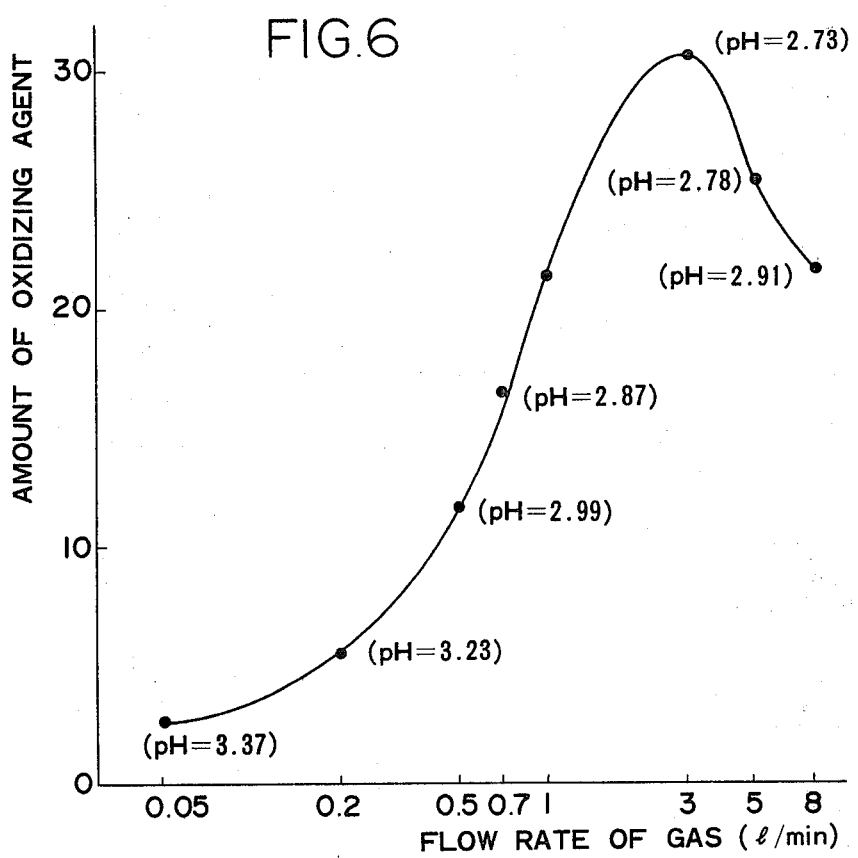
FIG. 6 is a graph showing a relationship between amount of the oxidizing agent produced and flow rate of a mixture of oxygen ($O_2$) and ozone ($O_3$)

2% by weight aqueous solution of PEG 20,000 was treated with a mixed gas of $O_3$ and $O_2$ for 2 hours under the condition that the flow rate of $O_2$ to be introduced into the ozone generator was changed to 50 ml/min to 8 l/min. After remaining ozone was discharged from the reaction vessel, an amount of the oxidizing agent produced was measured by iodometric titration. The results are shown in FIG. 6 wherein each numeral noted at the dot for the measured amount of the oxidizing agent means the pH value of the solution.

These results show that the amount of the oxidizing agent produced is maximum substantially at the flow rate of oxygen of 3 l/min and decreases as the flow rate of oxygen decreases or increases therefrom. The pH value of the solution is higher as the amount of the oxidizing agent is lesser, which shows that the oxidization reaction does not sufficiently develop. The reasons why the amount of the oxidizing agent decreases under the flow rate of oxygen above 3 l/min are supposed to be that the reaction temperature is lowered due to a cooling effect by gases flowing into the reaction vessel, that the amount of ozone ($O_3$) produced in the ozone generator decreases as the flow rate of oxygen ($O_2$) increases, and that the chance for ozone ($O_3$) to contact with the liquid in the reaction vessel is lesser when the flow rate of gases supplied into the liquid is in excess of a certain value.

§ Treating time by $O_3$ and amount of oxidizing agent manufactured from PEG 20,000

As described above, the yield of the oxidizing agent was good in the case that the flow rate of the mixed gas of $O_3$ and $O_2$ was about 3 l/min. For this reason, the yield of the oxidizing agent dependent on the treating time was measured when the solution of PEG was treated under that flow rate. That is, 2% by weight solution of PEG 20,000 was treated at 90° to 100° C. for 1 to 10 hours under the condition that a mixed gas of $O_3$ and $O_2$ was blown into the solution at a flow velocity of 3 l/min.

Figure 7:
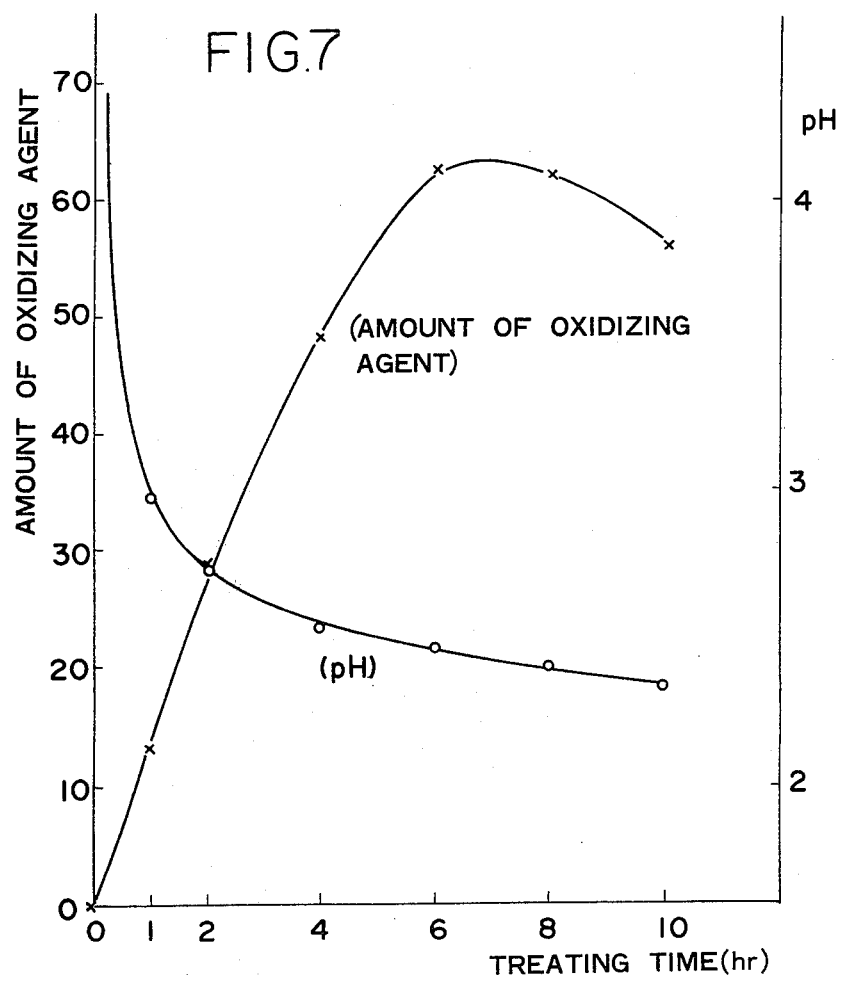
FIG. 7 is a graph showing respective change of amount of the oxidizing agent produced and pH value of the solution in dependence on a treating time by a mixture of oxygen ($O_2$) and ozone ($O_3$)

According to the results shown in FIG. 7, it will be recognized that the amount of the oxidizing agent produced is maximum in the range of the treating time, of 6 to 8 hours. It will be also recognized that the pH value of the solution at the treating time of 8 hours and 10 hours is lesser than that at lesser treating time, whereas the amount of the oxidizing agent decreases progressively from the maximum. It is supposed from this result that the oxidation reaction at the treating time of 8 hours and 10 hours develops more than that at the treating time of 6 hours.

§ Concentration of raw PEG and yield of oxidizing agent

The influence of the concentration of the aqueous raw PEG 20,000 solution on the yield of the oxidizing agent was studied. That is, after 1 to 50% by weight aqueous solution of PEG 20,000 was heated to about 100° C., a mixed gas of $O_3$ and $O_2$ was introduced into the solution at a rate of 3 l/min for 2 hours, and remaining $O_3$ in the vessel was discharged before the solution was cooled.

Figure 8:
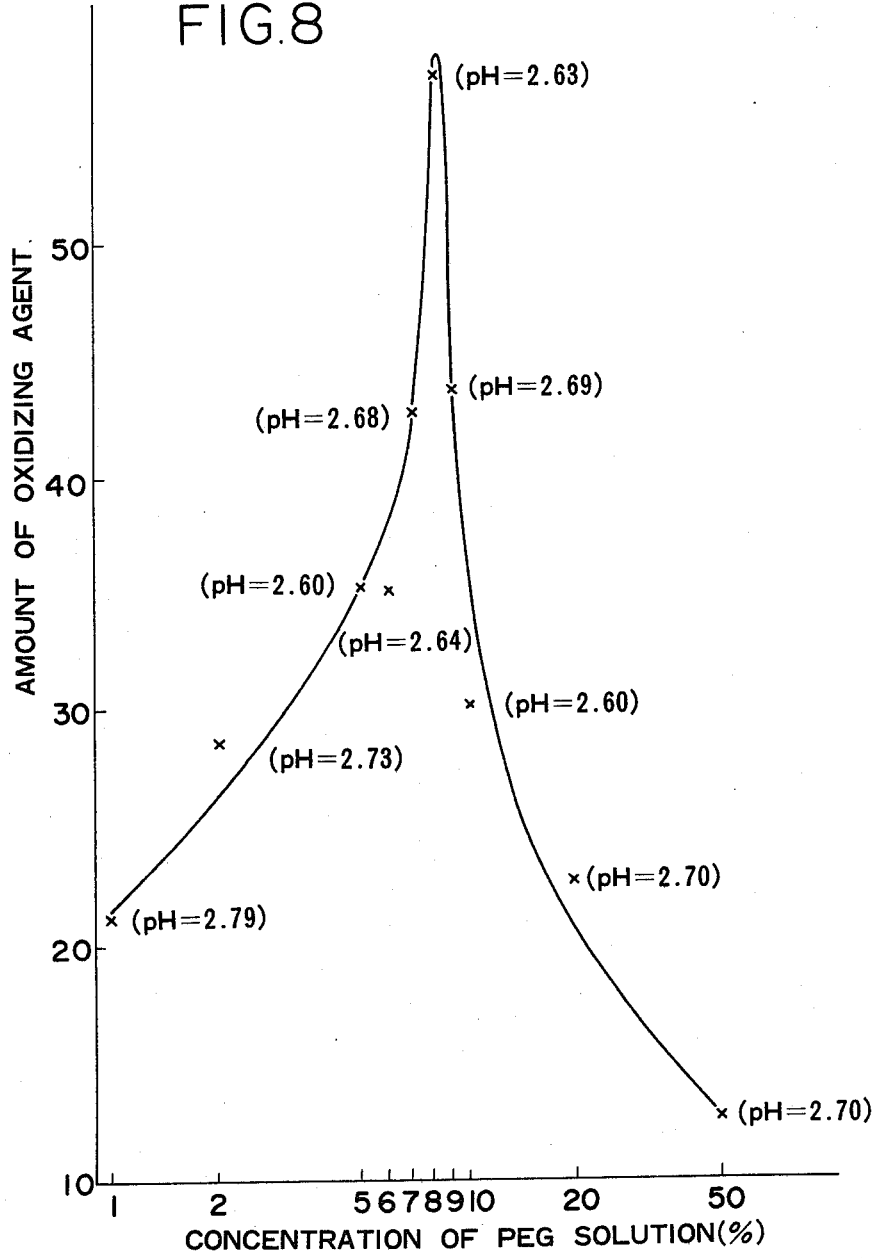
FIG. 8 is a graph showing a relationship between amount of the oxidizing agent produced and concentration of raw polyethylene glycol.

The yield of the oxidizing agent is shown in FIG. 8 in which each numeral noted at the dots showing the amount of the oxidizing agent means the pH value of the solution measured after the reaction. It can be understood that the yield of the oxidizing agent after the reaction for 2 hours is the best when the concentration of PEG is about 8% by weight. The reason why the yield of the oxidizing agent becomes lesser in the concentration of PEG above 8% by weight are supposed to be that a solubility of $O_2$ or $O_3$ to the solution decreases, a self-oxidation-reduction reaction occurs, a reaction time is poorer and so on.

Figure 9:
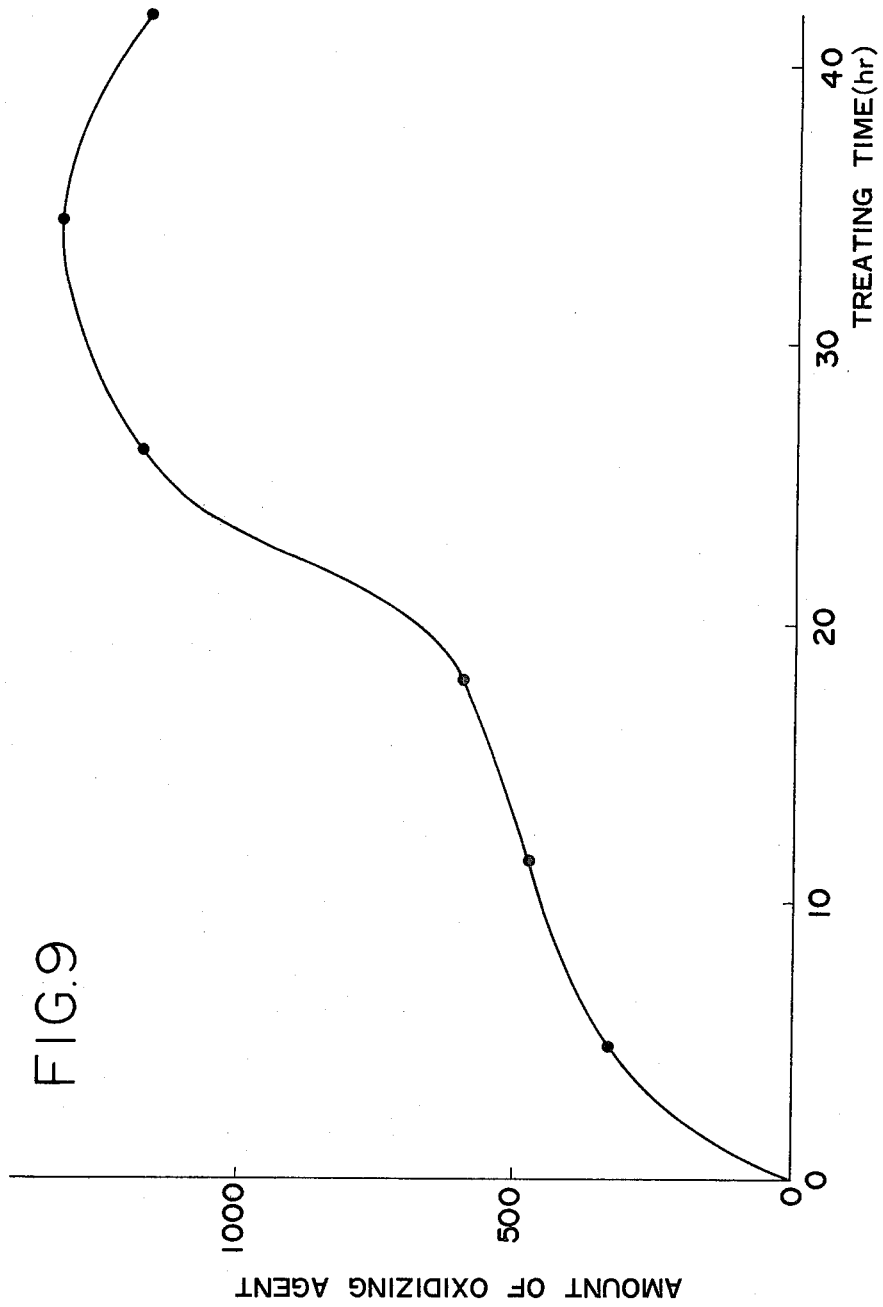
FIG. 9 is a graph showing a relationship between amount of the oxidizing agent produced and a treating time in the case that a concentration of raw polyethylene glycol is 100%.

It was also found out that the oxidizing agent was produced with high yield even when no water as a solvent was added to PEG, that is, melted PEG having a concentration of 100% was used. In this case, 32.3 g of PEG 20,000 was received in a flask having a volume of 300 ml and then melted by hot water bath. When the temperature of the melted PEG was kept at 60° to 70° C. and a mixed gas of $O_3$ and $O_2$ at a rate of 300 ml/min was introduced thereinto, the results shown in FIG. 9 about the relationship of the treating time and the amount of the oxidizing agent were obtained. The change of the amount of the oxidizing agent shown in FIG. 9 is significantly similar to that shown in FIG. 2, which means that the mechanism of the production of the oxidizing agent is substantially the same in both cases shown in FIG. 9 and FIG. 2. FIG. 9 shows also that the melted PEG having a concentration of 100% results in an improved yield of the oxidizing agent which is larger one figure than that shown in FIG. 8. In the case shown in FIG. 9, the sample of the oxidizing agent at the time when more than 11 hours and 30 minutes after the beginning of the oxidation treatment was in a liquid state at a room temperature. On the other hand, also when melted polypropylene glycol having a concentration of 100% was used and oxidized by the same way, oxidizing agent could be produced with good yield.

Judging from these results, a permissible range of the concentration of PEG in the manufacturing of the oxidizing agent should not be limited to that shown in FIG. 8 and the upper limit of the concentration may be high as much as possible. The lower limit of the concentration is practically 1% by weight. Though PEG or polypropylene glycol to be used has a solidifying point of less than 100° C., these become liquid at a room temperature as the oxidation reaction develops. Accordingly, the use of a concentration of 100% PEG or solid PEG causes no problem because it becomes liquid on the oxidation reaction. For this reason, either PEG in an aqueous state (an aqueous solution of PEG) or PEG in a melter state (a melted PEG) can be used for manufacturing the oxidizing agent.

§ Treating temperature and yield of oxidizing agent

8% by weight aqueous solution of PEG 20,000 was treated with a mixed gas of $O_3$ and $O_2$ for 2 hours under the condition that the flow rate of the mixed gas was 3 l/min and the treating temperature was varied in the range from a room temperature to 100° C.

Figure 10:
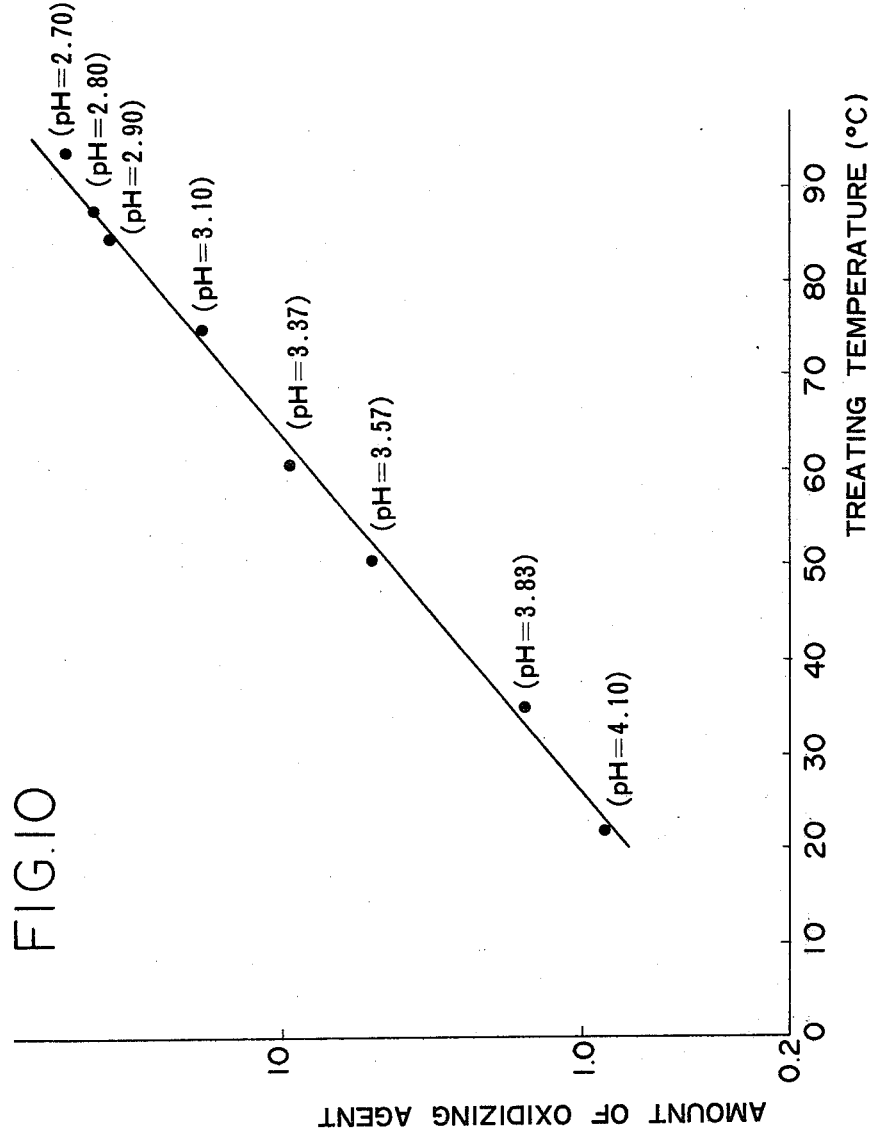
FIG. 10 is a graph showing a relationship between amount of the oxidizing agent produced and a treating temperature for the raw polyethylene glycol.

The yield of the oxidizing agent produced is shown in FIG. 10 in which each numeral noted at the dots showing the amount of the oxidizing agent means the pH value of the solution. According to the results shown in FIG. 10. it can be understood that the yield of the oxidizing agent increases like an exponential function as the temperature rises, FIG. 10 also shows that the yield of the oxidizing agent is improved when the pH value of the solution is low, which suggests that the yield of the oxidizing agent can increases by the treatment for longer treatment or at a higher temperature.

§ Influence of irradiation of visible rays on yield of oxidizing agent

2% by weight and 8% by weight solutions of PEG 20,000 were treated with oxygen ($O_2$). It was measured whether or not the yield of the oxidizing agent produced was influenced by the irradiation of visible rays. The conventional fluorescent lamp was used as a light source for the visible rays. The result for the sample which was irradiated by the visible rays was obtained in comparison with that which was not irradiated by the visible rays. In this experiment, each solution was treated with oxygen ($O_2$) which was introduced thereinto at a rate of 3 l/min, for 1 hour, 2 hours and 4 hours respectively.

Both results with and without the irradiation of visible rays do not almost differ from each other. For example, when the solutions were treated for 1 hour at the treating temperature of 85° to 86° C., the yield of the oxidizing agent was 1.47 in the case of the irradiation of visible rays and 1.40 in the case of no irradiation of visible rays. The pH value of the solution after the oxidation was 4.27 in both cases. When the solutions were treated for 4 hours at the same temperature as that described above, the yield of the oxidizing agent and the pH value of the solution were 26.1 and 4.87 respectively in the case of the irradiation of visible rays, and 24.2 and 4.68 respectively in the case of no irradiation of visible rays.

§ Influence of irradiation of ultraviolet rays on yield of oxidizing agent

8% by weight solution of PEG 20,000 was treated with $O_3$ or $O_2$ under the irradiation of ultraviolet rays. It was measured whether or not the yield of the oxidizing agent produced was influenced by the irradiation of ultraviolet rays. A mercury lamp was used as a light source.

The yield of the oxidizing agent was not almost influenced by the irradiation or no irradiation of ultraviolet rays. That is, when oxygen ($O_2$) at a rate of 3 l/min was introduced into the solution at a temperature of about 86° C. for 2 hours, the amount of the oxidizing agent produced was 8.70 in the case of the irradiation of ultraviolet rays and 8.72 in the case of no irradiation of ultraviolet rays. When a mixed gas of $O_3$ and $O_2$ was introduced into the solution for 2 hours under the same conditions as those decribed above, the amount of the oxidizing agent produced was 43.9. This amount does not substantially differ from the amount (40.0) which can be read at the temperature of about 86° C. in FIG. 10.

§ Influence of catalyst on yield of oxidizing agent

The oxidizing agent was produced under the condition that a few kinds of metal and $CuSO_4$ were added to the solution of PEG. The change of the yield of the oxidizing agent was measured. For example, 2% by weight and 8% by weight solutions of PEG 20,000 were treated with oxygen ($O_2$) at a rate of 3 l/min for 2 hours under the addition of Ag, Pt or Au as the conventional oxidizing catalyst to the solution.

The amount of the oxidizing agent produced under the addition of the metal did not substantially differ from that under no addition of the metal. When $10^{-4}$ mol $CuSO_4$ solution was added to 1 l of 2% by weight solution of PEG 20,000 and 3 l/min oxygen ($O_2$) was introduced thereinto, data showing a promotion of oxidation reaction by the addition of $CuSO_4$ could not be obtained.

§ pH value of raw PEG solution and amount of oxidizing agent produced

The pH value of 8% by weight solutions of PEG 20,000 was changed in the range from 6.62 to 11.23. Each solution was treated with a mixed gas of $O_3$ and $O_2$. The yields of the oxidizing agent in the resulting liquid and the pH values of the resulting liquid were measured. That is, NaOH was added to the solution of raw PEG 20,000 having a pH value of 6.62 to adjust the pH value of the solution to 7.00, 8.16, 8.93, 10.11 and 11.23 respectivey. The solutions having these pH values were treated with the mixed gas of $O_3$ and $O_2$ at a rate of 3 l/min for 2 hours.

The resulting solutions had a constant pH value in the range from 2.72 to 2.80 and the amount of the oxidizing agent produced flactuated merely in the range from 50.9 to 62.8. The amount of the oxidizing agent produced had almost no relation with the pH value of the starting solution of PEG, which is supposed to be based upon a reason that the pH value of the solution at the initial stage was compensated with carboxylic acid produced by the oxidation reaction so that the amount of the oxidizing agent was not influenced by the pH value of the starting solution.

§ pH value and oxidizing power of oxidizing agent

The influence of the pH value of the oxidizing agent on its oxidizing power was measured. 0.1 N NaOH was added to each 5 ml of the oxidizing agent solution having a pH value of 2.38 and an amount of the oxidizing agent of 11.58 so as to change the pH value to that in the range from 3.00 to 11.57. After each solution was then left for 3 days at a room temperature, 10 ml of 0.1 mol KI solution was added thereto to titrate isolated iodine by 0.01 mol $Na_2S_2O_3$ solution.

According to the result shown in FIG. 11, the amount of the oxidizing agent produced decreases abruptly in the range of the pH value of 4 to 5. It can be accordingly understood that the pH value of the oxidizing agent solution should be below 5 to obtain a preferable oxidizing power. Potassium phthalate was added to the oxidizing agent solution having a pH value of 6 to 10 to decrease the pH value, however, the oxidizing power of the oxidizing agent did not increase.

§ Use of other kinds of alcohols as raw material

It was examined whether or not oxidizing agent was produced from other kinds of alchols except PEG by the same way as the case of the use of PEG.

(1) Use of high molecular substance as raw material

There was prepared each 2% by weight solution of polypropylene glycol having an average molecular weight of 2,000 (PPG 2,000), oleic acid ester of polyoxyethylene sorbitan (Twin 80 on sale as a surface active agent), and polyvinyl alcohol having an average molecular weight of 20,000 (PVA 20,000). Each of these solution was treated for 2 hours by introducing oxygen ($O_2$) thereinto. KI solution was then added to each solution.

As a result, the solution resulting from PPG 2,000 or Twin 80 as a starting material isolated iodine ($I_2$), however, the solution resulting from PVA 20,000 did not exhibit an oxidizing power. When each solution of PPG 2,000, Twin 80 and PVA 20,000 was treated with a mixed gas of $O_3$ and $O_2$ for 2 hours, the solution resulting from PPG 2,000 or Twin 80 isolated iodine ($I_2$) more violently than the treatment with oxygen ($O_2$), however, the solution resulting from PVA 20,000 exhibited no oxidizing function of an oxidizing agent. On the other hand, when the solution of PVA 20,000 was treated with a mixed gas of $O_3$ and $O_2$ for 5 hours, a small amount of oxidizing agent having an oxidizing power could be obtained.

A semiconductor material, for example, GaAs was immersed into the oxidizing agent solutions produced to be thermally treated. As result, an oxidized layer was formed on the surface of GaAs in any cases. It will be evident that the oxidizing agent can be produced in any cases, though the amount of it is lesser than that which is obtained by the use of PEG 20,000.

(2) Use of polyhydric alcohol (monomer) as raw material

Each 2 to 5% by weight solution of propylene glycol, ethylene glycol. glycerine, sorbitol, mannitol and saccharose was treated with a mixed gas of $O_3$ and $O_2$ for 2 hours. Oxidizing agent could not be almost produced in any cases.

This fact shows that bonding chains of polymer such as PEG are cut off by the oxidation reaction to form new chemical structures in the process of the production of the oxidizing agent.

§ Use of oxidizing agent manufactured from PEG

The oxidizing agent manufactured from PEG is water-soluble and stable at a room temperature. The oxidizing agent can be accordingly used as a surface-treatment agent for metals or semiconductors, a bleaching agent, a dyeing assistant, a disinfectant, a sterilizing agent, a detergent and so on. Several knowledges about the surface treatment agent and the bleaching agent could be obtained, which will be briefly described as follows:

(1) Surface treatment for semiconductor

The oxidizing agent manufactured from 2% by weight solution of PEG 2,000 as a starting material was heated to 90° to 100° C. When GaAs was immersed into the heated oxidizing agent to be treated, an oxidized layer having a uniform thickness of 1,000 to 3,000Å was formed on GaAs in a time from a few minutes to a few tens of minutes. An oxidized layer having a thickness of 7,000 to 8,000 Å was grown on GaAs by the treatment time of a few hours. It was also found that the growing velocity of the oxidized layer was not almost influenced by the crystal face directions of GaAs, however, it was influenced by the specific resistivity of GaAs so that an oxidizing velocity of an insulating substrate by the oxidizing agent was slow. According to a measurement of a chemical composition of the oxidized layer by EPMA (Electron Probe Microanalyzer), carbon atoms combining with the oxidizing layer could not be found.

The oxidation method by the use of the oxidizing agent of this invention is remarkably superior in view of the growing velocity and the uniform thickness of the oxidized layer in comparison with the conventional known chemical oxidation method. This reason is supposed to be based upon also the fact that an angle of contact of the oxidizing agent solution to GaAs is considerably smaller than that of pure water.

On the other hand, when InSb was treated in the oxidizing agent solution manufactured from 2% by weight solution of PEG 2,000 as a starting material, an oxidized layer was also formed thereon.

(2) Surface treatment for metal

An aluminium foil was immersed into the oxidizing agent manufactured from 2% by weight solution of PEG 4,000 as a raw material. The aluminium foil was then heated in the oxidizing agent. As a result, a transparent oxidized layer having interference color could be obtained by the treatment of 1 hour and a white oxidized layer could be obtained by the treatment of 3.5 hours.

Besides, a cooper plate was immersed into the same oxidizing agent solution and treated for 8 hours. A surface chemical composition of the copper plate which was then identified by an X-ray diffractometer conformed with $Cu_2O$.

(3) Bleaching function

Hairs of human and fibers of hemp palm were immersed into the oxidizing agent manufactured from 2% by weight solution of PEG 2,000 as a raw material. When the hairs and the fibers were then thermally treated in the oxidizing agent for 1 hour, they turned somewhat red in comparison with those which were not treated. Besides, they were immersed into the oxidizing agent manufactured from 8% by weight solution of PEG as a starting material and were left for one month at a room temperature. Also in this case, the hairs and the fibers showed a similar change of color to that described above.

In order to examine the action of the oxidizing agent on a fraction of foods which had sticked on a fibrous article, a sterilized gauze was immersed into black tea, coffee, sauce or soy. The gauze was then taken out therefrom after one hour had passed and was sufficiently washed by water before dried by air-dry. Thus contaminated gauze was treated with the oxidizing agent heated at abour 80° C. and manufactured from PEG for 2 minutes, the oxidizing agent at a room temperature manufactured from PEG for 12 hours, or the conventional hydrogen peroxide solution (Oxyful on sale manufactured Sankyo Corp.) at a room temperature for 2 hours. The gauze was then washed by water before dried. Each contaminated gauze was bleached and exhibited a quite similar tone of color when seen with the naked eye. According to a similar experiment wherein the contaminated gauze was not dried and treated with the oxidizing agents or Oxyful solution described above, it was also bleached and exhibited a quite similar result. Also when the gauze was subjected to a bleaching test by the oxidizing agent which had been manufactured 8 months before and then left, a quite similar result was obtained.

§ Characteristics of oxidizing agent manufactured from PEG (1) Stability at a room temperature and function with delayed effect As described above, the oxidizing agent solution was stable even when it was left for a few months at a room temperature. The concentration of the oxidizing agent solution was measured every one month after it had been manufactured. As a result, the concentration did not show a particular flactuation even after 10 months had passed.

2% by weight solution of PEG 6,000 which had treated with oxygen ($O_2$) for 2 hours was subjected to a boiling treatment by blowing no gas thereinto. A part of the solution was taken out after 2 hours and a KI solution was added thereto. Iodine ($I_2$) was isolated from the solution in a lesser amount than that obtained before the oxidizing agent solution was thermally treated. When the oxidizing agent was further subjected to the boiling treatment for 1.5 hours, the amount of the oxidizing agent further decreased, however, its oxidizing power was still maintained. Accordingly, if an article or substance is oxidized by the oxidizing agent, the oxidation reaction develops very slowly at a room temperature, and the heating of the oxidizing agent is required for a rapid treatment. Even if the oxidizing agent solution was contacted with the skin and the like at a room temperature, no injury could not be found.

(2) Very easy and safe method of manufacturing oxidizing agent with low cost

As described in the item (1), the oxidizing agent can be produced by a very easy way that $O_2$ or $O_3$ has only to be blown into the aqueous solution of PEG. Therefore, any operators can produce the oxidizing agent by the use of a raw material of low cost and of the device generally used. Because the oxidizing agent can be produced by gas-liquid reaction, it is considered that also the oxidation under a high pressure is effective.

(3) Non-poisonous and harmless oxidizing agent

The function on the human body, for example, a poisonousness of the oxidizing agent must be discussed on the basis of physiological and medical data. However, the oxidizing agent of this invention can be expected to be non-poisonous and harmless according to the facts that a structural unit of nonionic surface active agent being used as a raw material for cosmetics and pharmacy is used as a starting material, that the oxidizing agent is stable at a room temperature and water-soluble, that the oxidizing agent tends to gradually decompose when left in the natural world, and so on. In order to examine the characteristics of the decompositon property in the natural world, earth was received in a beaker having a volume of 500 ml and the oxidizing agent solution was added thereto to the extent that liquid component was somewhat isolated. The oxidizing agent in the beaker was then left and each part of the liquid in the beaker was taken out after one day, one week and one month to measure the amount of remaining oxidizing agent. As a result, it was found that the amount of the remaining oxidizing agent gradually decreased and disappeared after one month.

(4) Water-soluble property

Because the oxidizing agent is water-soluble, it can be used for various reactions and uses.

The oxidizing agent solution is more wettable to various kinds of metals and semiconductors, plants, living body such as the skin and the hair than pure water. It is supposed that this fact further spreads the use of the oxidizing agent. As described above, in practical, the surface treatment of GaAs by the oxidizing agent results in a formation of the oxidized layer thereon having a uniform thickness which can not be achieved by the conventional oxidation with oxygen existing in a water bath.

It will be evident that various modifications can be made to the described embodiments without departing from the scope of this invention.

What is claimed is:

1. A method of manufacturing an oxidizing agent containing an organic peroxide compound comprising the step of oxidizing an aqueous solution containing as its sole oxidizable agent more than 1% by weight of a polyoxyalkylene polyether, or a melted polyoxyalkylene polyether by introducing an oxidizing gas consisting of oxygen and ozone thereinto at a temperature between 50° and 100° C., said polyoxyalkylene polyether having an average molecular weight of 1,000 to 30,000 and being represented by the following general forumla:

where R stands for an alkylene group represented by a general forumula $(CH_2)_m$ where $m=2$ or 3.

* * * * *